United States Patent
Chu et al.

(10) Patent No.: US 9,826,759 B2
(45) Date of Patent: Nov. 28, 2017

(54) AVENANTHRAMIDE-ENRICHED OAT PRODUCT

(71) Applicant: THE QUAKER OATS COMPANY, Chicago, IL (US)

(72) Inventors: YiFang Chu, Glenview, IL (US); Jodee Johnson, Lake in the Hills, IL (US); Marianne O'Shea, Chicago, IL (US); Yuhui Shi, Schaumburg, IL (US)

(73) Assignee: The Quaker Oats Company, Chicago, IL (US)

( * ) Notice: Subject to any disclaimer, the term of this patent is extended or adjusted under 35 U.S.C. 154(b) by 803 days.

(21) Appl. No.: 14/284,101

(22) Filed: May 21, 2014

(65) Prior Publication Data

US 2015/0335045 A1 Nov. 26, 2015

(51) Int. Cl.
| | |
|---|---|
| *A23L 1/168* | (2006.01) |
| *A23K 1/16* | (2006.01) |
| *A61K 31/196* | (2006.01) |
| *A23L 7/143* | (2016.01) |
| *A23L 33/00* | (2016.01) |

(52) U.S. Cl.
CPC ............ *A23K 1/1612* (2013.01); *A23L 7/143* (2016.08); *A23L 33/00* (2016.08); *A61K 31/196* (2013.01); *A23V 2002/00* (2013.01)

(58) Field of Classification Search
CPC ......... A23K 7/143; A23L 33/00; A23L 7/143; A61K 31/196; A23V 2002/00
See application file for complete search history.

(56) References Cited

U.S. PATENT DOCUMENTS

| | | | |
|---|---|---|---|
| 9,504,272 B2 * | 11/2016 | Carder | ................. A23L 2/02 |
| 2005/0042243 A1 | 2/2005 | Redmond | |
| 2006/0100274 A1* | 5/2006 | Meydani | .............. A61K 31/195 514/534 |
| 2010/0267662 A1 | 10/2010 | Fielder | |
| 2012/0082740 A1* | 4/2012 | Collins | ................ A61K 36/899 424/750 |
| 2013/0183405 A1 | 7/2013 | Chatel | |
| 2013/0209610 A1 | 8/2013 | Carder | |

OTHER PUBLICATIONS

Mackevic Swedish University of Agricultural Science, 2010, downloaded from http://stud.epsilon.slu.se/830/ 17 pages.*
Karin Jonsson Swedish University of Agricultural Sciences, 2006 downloaded from https://pingpong.ki.se/public/pp/public_courses/course06909/published/1289756174391/resourceId/3956878/content/infoweb/node-74255/karin_jonsson.pdf 10 pages.*
International Search Report and Written Opinion, PCT/US2015/032025, dated Sep. 17, 2015, 9 pages.

(Continued)

*Primary Examiner* — Chhaya Sayala
(74) *Attorney, Agent, or Firm* — James R. Gourley; Stephen Y. Liu; Carstens & Cahoon, LLP

(57) ABSTRACT

A composition and method for an avenanthramide-enriched, oat-based product having improved health effects. The oat-based product includes an avenanthramide ingredient having avenanthramides 2c:2p:2f in ratios comprising at least one of 1:1:1 or 1:2:2. More particularly, the avenanthramide ingredient may be derived synthetically or recovered from processing raw oats into constituent oat fractions.

14 Claims, 2 Drawing Sheets

| OAT FRACTIONS | AVENANTHRAMIDE CONTENT (mg/kg) | | | | AVENANTHRAMIDE RATIO | | |
|---|---|---|---|---|---|---|---|
| | 2C | 2P | 2F | TOTAL | 2C | 2P | 2F |
| HULLS | 1.84 | 1.87 | 1.57 | 5.28 | 1 | 1 | 1 |
| TRICHOMES | 9.24 | 21.5 | 24.54 | 55.28 | 1 | 2 | 3 |
| FLOUR | 26.19 | 19.57 | 60.39 | 106.15 | 1 | 1 | 2 |

(56) References Cited

OTHER PUBLICATIONS

Collins, F.W., "Oat Phenolics: Avenanthramides, Novel Substituted N-Cinnamoylanthranilate Alkaloids from Oat Groats and Hulls," J. of Agricultural and Food Chemistry, Jan.-Feb. 1989, vol. 37(1), pp. 60-66 (7 pages).

Bratt, K., et al., "Avenanthramides in Oats (*Avena sativa* L.) and Structure—Antioxidant Activity Relationships," J. of Agricultural and Food Chemistry, Jan. 29, 2003, vol. 51(3), pp. 594-600 (7 pages).

Emmons et al., Antioxidant Capacity of Oat (*Avena sativa* L.) Extracts. 2. In Vitro Antioxidant Activity and Contents of Phenolic and Tocol Antioxidants, JJ. Agric. Food Chem., 1999, vol. 47, pp. 4984-4898, American Chemical Society, 5 pages.

Handelman et al., Antioxidant Capacity of Oat (*Avena sativa* L.) Extracts. 1. Inhibition of Low-Density Lipoprotein Oxidation and Oxygen Radical Absorbance Capacity, J. Agric. Food Chem., 1999, vol. 47, pp. 4888-4893, American Chemical Society, 6 pages.

Peterson et al., Oat avenanthramides exhibit antioxidant activities in vitro, Food Chemistry, vol. 79, pp. 473-478, Elsevier Science Ltd., 2002, 6 pages.

Liu et al., The antiatherogenic potential of oat phenolic compounds, Artherosclerosis, vol. 175, pp. 39-49, Elsevier Ireland Ltd., 2004, 11 pages.

Chen et al., Avenanthramides and Phenolic Acids from Oats Are Bioavailable and Act Synergistically with Vitamin C to Enhance Hamster and Human LDL Resistance to Oxidation1,2, The Journal of Nutrition, pp. 1459-1466, American Society for Nutritional Sciences, 2004, 8 pages.

Chen et al., Avenanthramides Are Bioavailable and Have Antioxidant Activity in Humans after Acute Consumption of an Enriched Mixture from Oats1,2, The Journal of Nutrition, pp. 1375-1382, American Society for Nutrition, 2007, 8 pages.

Guo et al., Avenanthramides, polyphenols from oats, inhibit IL-1β-induced NF-κB activation in endothelial cells, Free Radical Biology & Medicine, vol. 44, pp. 415-429, Elsevier, Inc., 2007, 15 pages.

Lee-Manion et al., In Vitro Antioxidant Activity and Antigenotoxic Effects of Avenanthramides and Related Compounds, J. Agric. Food Chem., vol. 57, pp. 10619-10624, 2009, 6 pages.

Sen et al., Antioxidant Effects of Oats Avenanthramides on Human Serum, Agricultural Sciences in China, vol. 10(8), pp. 1301-1305, Elsevier Ltd., 2011, 5 pages.

Meydani et al., Avenanthramides, unique polyphenols of oats with potential health effects, John Wiley & Sons, Ltd., 2014, 10 pages.

\* cited by examiner

| OAT FRACTIONS | AVENANTHRAMIDE CONTENT (mg/kg) | | | | AVENANTHRAMIDE RATIO | | |
|---|---|---|---|---|---|---|---|
| | 2C | 2P | 2F | TOTAL | 2C | 2P | 2F |
| HULLS | 1.84 | 1.87 | 1.57 | 5.28 | 1 | 1 | 1 |
| TRICHOMES | 9.24 | 21.5 | 24.54 | 55.28 | 1 | 2 | 3 |
| FLOUR | 26.19 | 19.57 | 60.39 | 106.15 | 1 | 1 | 2 |

AVENANTHRAMIDE-ENRICHED OAT PRODUCT

BACKGROUND OF THE INVENTION

Technical Field

The present invention relates generally to an oat-based product with improved health effects. More particularly, an oat-based product is enriched with avenanthramides of the 2c, 2p, and 2f moieties at pre-determined ratios to achieve either an improved anti-inflammatory effect or antioxidant effect.

Background

Oats are a cereal grain that can be processed and separated into constituent fractions that include oat groats, hulls, and trichomes. Each of these oat fractions is utilized differently. For example, the hull and trichome fractions are commonly considered by-products undesirable for human consumption. As a result, these oat fractions are sometimes incorporated into livestock feed, or further processed into different products altogether, such as biomass fuel. In contrast, oat groats are commonly consumed. To prepare the oat groats for consumption, they may be rolled or ground into oatmeal and eaten as a breakfast food, incorporated as an ingredient in another oat-based product, or they may be ground into flour that is then used to create the oat-based product. Non-limiting examples of oat-based products include cookies, bread, or cold cereals, such as muesli and granola.

SUMMARY OF THE INVENTION

The present invention generally provides a composition and method for producing an avenanthramide-enriched, oat-based product with identifiable and improved health effects. This invention further provides for a method of producing the avenanthramide-enriched, oat-based product to achieve at least one of an improved antioxidant effect or an anti-inflammatory effect.

The inventors have investigated and quantified the in vitro effects of avenanthramides using nuclear factor-kappa B (NF-κB) assays and Oxygen Radical Absorbance Capacity (ORAC) assays. The results of these experiments have shown that the quantity of avenanthramides do not control the expression of the beneficial health effects. Specifically, oat fractions having the highest avenanthramide concentration did not necessarily achieve the highest benefit, as confirmed by various in vitro tests. Instead, the ratio of the three most abundant types of avenanthramides in oats dictated the overall effect. These three avenanthramides are hydroxy anthranilic (2) acid conjugated with p-coumaric (p), caffeic (c) or ferulic (f) moieties, thus named 2p, 2c, and 2f, respectively. Thus, based on the results of their research, inventors have created a novel oat-based product and method of production, as disclosed herein.

In a first aspect of the invention, a product is provided that comprises specific ratios of avenanthramides 2c:2p:2f for achieving a selected health benefit. In a first embodiment of the first aspect, an oat-based product with an avenanthramide ingredient having 2c:2p:2f in the ratio of about 1:2:2 yields optimal anti-inflammatory effects. In a second embodiment, an oat-based product with an avenanthramide ingredient having 2c:2p:2f in the ratio of about 1:1:1 yields optimal antioxidant effects.

In a second aspect, the present invention provides a method for creating an avenanthramide-enriched, oat-based product having improved health effects. This method generally includes the steps of deriving an avenanthramide ingredient having a pre-selected ratio of 2c:2p:2f, then adding the avenanthramide ingredient to the oat-based product to achieve a predetermined health effect. In a first embodiment the derivation of the avenanthramide ingredient includes the steps of processing raw oats into its constituent fractions, which includes at least one of an oat trichome fraction and an oat hull fraction. Additionally, the adding step of this first illustrative embodiment comprises adding one of the oat trichome or the oat hull fractions to the oat-based product to achieve a selected health effect.

As used herein, the phrase "at least one of," when applied to a list, means any combination of list items. Thus, "processing raw oats into its constituent fractions, which includes at least one of an oat trichome fraction and an oat hull fraction" means that the constituent fractions can be either the oat trichome fraction, or the oat hull fraction, or both the oat trichome fraction and the oat hull fraction.

In a second illustrative embodiment of the second aspect, the step of deriving an avenanthramide ingredient comprises creating a synthesized avenanthramide ingredient having 2c:2p:2f in a ratio of about 1:1:1 or about 1:2:2. The adding step of this second illustrative embodiment comprises adding the synthesized avenanthramide ingredient to an oat-based product.

The creation of oat-based products using the methods described herein allow manufacturers the ability to more efficiently utilize oats by reducing waste, and create products having specific health benefits. Consumers would thus have the option to purchase and consume enriched, oat-based products that improve aspects of their health and well-being.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figures 1, 4:
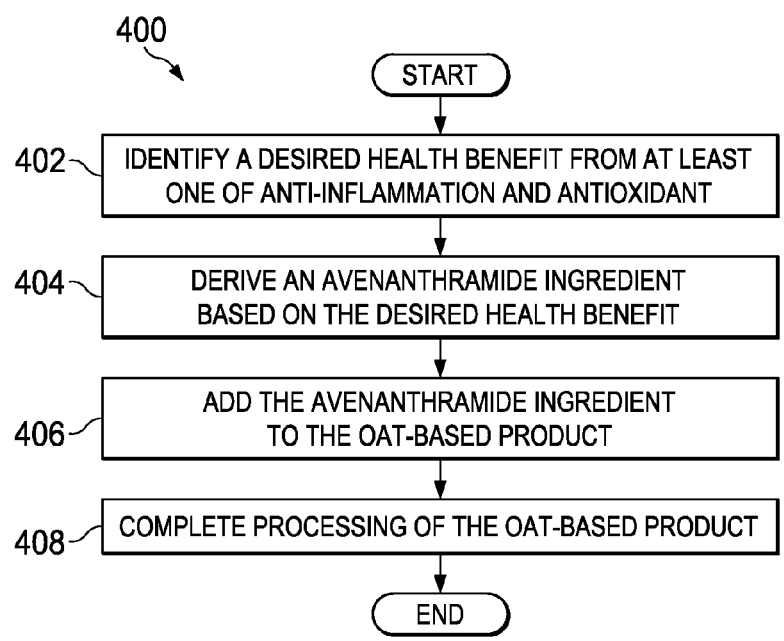
FIG. 1 is a table illustrating avenanthramide content and ratios in oat hulls, trichomes, and flour.
FIG. 4 is a flowchart of a process for producing an avenanthramide-enriched, oat-based product in accordance with an illustrative embodiment.

Oats are cereal grains suitable for human consumption, commonly in the form of oatmeal. Alternatively, they may be used as an ingredient in forming oat-based products, such as granola bars and the like. Oat-based products have recently experienced a resurgence in popularity as a result of the increasing number of studies documenting health benefits derived from consuming oats, such as the promotion of healthy heart function. For example, the high soluble fiber content of oats, mainly in the form of β-glucan, provides oats the ability to reduce low-density lipoprotein (LDL) cholesterol levels by increasing the conversion of cholesterol to bile. Additionally, consumption of oats has been shown to prevent the development of atherosclerosis through inhibition of oxidative stress and inflammation.

Oxidative stress and inflammation also play critical roles in the pathogenesis of many diseases, such as cancer, arthritis, and obesity. Suppression of oxidative stress and inflammation are therefore key steps in preventing disease formation. With regard to oxidative stress, which manifests as cellular damage caused by reactive oxygen species, the introduction of antioxidants terminates harmful chain reactions set into motion by these unstable molecules. On the other hand, suppression of inflammation can be achieved through inhibition of NF-κB activity. Other known benefits of oat consumption include anti-proliferative, vasodilation, and anti-itch effects. These beneficial effects have been attributed to the presence of avenanthramides within the oats.

Avenanthramides are bioavailable, soluble phenolic compounds not present in other cereal grains. Synthesized avenanthramides or avenanthramides-enriched oat products have consistently shown potent antioxidant and anti-inflammatory efficacy in both in vitro and in vivo research. For example, an avenanthramide-enriched mixture has been shown to decrease pro-inflammatory cytokine production and adhesion molecule expression in human aortic endothelial cells (Liu et al., 2004). In another study, avenanthramide 2c had the highest antioxidant activity in vitro (Peterson et al., 2001). Likewise, consumption of 1 gram of an avenanthramide-enriched mixture by humans was shown to affect antioxidant status by increasing plasma glutathione (Chen et al., 2007). Because of these results, avenanthramide-rich oat brans have been added to oat flour to enhance its avenanthramide content. However, other outer layer fractions have been considered waste products and have not been incorporated into human comestibles.

Previously, attempts at creating avenanthramide-enriched oat products were predicated on the misconception that higher concentrations of avenanthramides yielded more favorable results. Although beneficial health effects can be realized using that method, a need exists for creating an avenanthramide-enriched oat product more efficiently and effectively, and which is specially tailored for selected health benefits.

Although avenanthramides are constitutively expressed in the kernels, the levels vary considerably in different oat fractions, with the highest concentration found in the bran and outer layers of the kernel. Oat flour, oat hulls, and trichomes are fractions with different ratios of the three most abundant avenanthramides. Unlike oat flour, the hulls and trichomes are currently considered waste products from oat processing; however both hulls and trichomes contain avenanthramides in varying concentrations. Investigating these differences may help with the development of new oat food products that provide greater and more beneficial health effects.

For the methods and products disclosed herein, oat hulls and trichomes were collected as waste-drain by-products from oat processing. Avenanthramide content (2c, 2p and 2f) was measured in oat flour, hulls and trichomes using reversed-phase high-performance liquid chromatography (HPLC) analysis. The peaks corresponding to avenanthramides 2c, 2p and 2f were quantified by comparing the obtained peak areas to those of standard curves. The avenanthramide ratios (2c:2p:2f) found in oat flour, hulls, and trichomes were determined based on their identified amounts in each oat fraction.

FIG. 1 is a table illustrating avenanthramide content and ratios in oat hulls, trichomes, and flour. The content and ratios of the three most abundant avenanthramides, namely the 2c, 2p, and 2f moieties, were measured in the various oat fractions and presented in FIG. 1. Oat flour was demonstrated to have the overall highest avenanthramide content with 106.15 mg/kg, followed by trichomes with 55.28 mg/kg, and then hulls with 5.28 mg/kg. Although it was previously known that different oat fractions contained different total amounts of avenanthramides, inventors discovered the unexpected finding that different oat fractions contain different ratios of the three most abundant avenanthramides. Specifically, the ratios of avenanthramides 2c:2p:2f for each of these oat fractions were calculated to be about 1:1:1 for hulls, about 1:1:2 for oat flour, and about 1:2:3 for trichomes.

To test the effect of varying avenanthramide ratios on antioxidant activity and inflammation in vitro, the inventors created an avenanthramide ingredient from pure avenanthramides which had similar ratios of avenanthramides 2c:2p:2f as was present in each of the three different oat fractions: hulls, flour, and trichomes. Thereafter, antioxidant activity was measured using the ORAC assay and anti-inflammatory effect was measured using an NF-κB inhibitory assay.

The first avenanthramide ingredient was created from 2c:2p:2f having a ratio of about 1:1:1, which corresponded to the concentration present in oat hulls. The second avenanthramide ingredient had avenanthramides 2c:2p:2f having a ratio of about 1:1:2, which corresponded to the concentration present in oat flour. Finally, the last avenanthramide ingredient tested had 2c:2p:2f in a ratio of about 1:2:2, which corresponded to the concentration present in oat trichomes. An ORAC assay was used to measure the antioxidant activity of each of these avenanthramide ingredients and the results are presented in Table 1.

TABLE 1

| Avenanthramide Ratio (2c:2p:2f) | ORAC (TE/g) |
| --- | --- |
| 1:1:1 | 37035.67 A* |
| 1:1:2 | 33382.33 B |
| 1:2:2 | 32988.67 B |

*Values with different letters are significantly different from each other ($p < 0.05$).

The highest antioxidant activity was exhibited by the first avenanthramide ingredient that has avenanthramides 2c:2p:2f in the ratio of approximately 1:1:1, at 37035.67 Trolox equivalents (TE)/g. Importantly, this ingredient had the highest relative concentration of avenanthramide 2c. As to the remaining two avenanthramide ingredients, the results indicate that decreasing concentrations of avenanthramide 2c is accompanied by an increased concentration of 2p and/or 2f, which results in decreasing antioxidant activity levels. Inventors believe that this effect can be explained by the fact that increased concentrations of avenanthramides 2p and 2f may be reducing or otherwise blocking the potency of avenanthramide 2c.

The antioxidant activity of each of the individual avenanthramides was also measured. The results are presented in Table 2, which confirm the understanding that avenanthramide 2c has the highest antioxidant activity in vitro out of the three most abundant avenanthramides. These results are consistent with at least one study presenting similar results (Peterson 2002).

TABLE 2

| Avenanthramide | ORAC (TE/g) |
|---|---|
| 2c | 33741.00 A* |
| 2p | 18504.33 B |
| 2f | 21812.67 B |

*Values with different letters are significantly different from each other ($p < 0.05$).

With these results, an enriched, oat-based product can be created with a pre-determined ratio of avenanthramides 2c:2p:2f to create a comestible having an optimized effect on antioxidant activity. A similar approach was used to determine the anti-inflammatory effects of the various ratios of avenanthramides 2c:2p:2f unique to oat hulls, flour, and trichomes. The results are discussed below in greater detail.

Using an NF-κB assay, the various oat fractions disclosed above were tested to determine their individual effects at inhibiting NF-κB activity. The results are tabulated in Table 3 and presented graphically in FIG. 2. With respect to Table 3, oat trichomes were shown to be the most effective at inhibiting NF-κB activity, with a 50% inhibitory concentration ($IC_{50}$) of 1.99 mg/mL. Oat flour was the next most effective fraction with an $IC_{50}$=3.21 mg/mL. Oat hulls were the least effective oat fraction at inhibiting NF-κB activity with an $IC_{50}$=8.70 mg/mL. These results indicate that overall avenanthramide content did not dictate the effectiveness of inhibiting NF-κB activity; instead, the particular ratio of avenanthramides 2c:2p:2f was controlling. For example, oat flour had the highest overall avenanthramide content but was only the second most effective oat fraction at inhibiting NF-κB activity.

TABLE 3

| Oat fractions | $IC_{50}$ (mg/mL) |
|---|---|
| Hulls | 8.70 A* |
| Trichomes | 1.99 B |
| Flour | 3.21 B |

*Values with different letters are significantly different from each other ($p < 0.05$).

Figure 2:
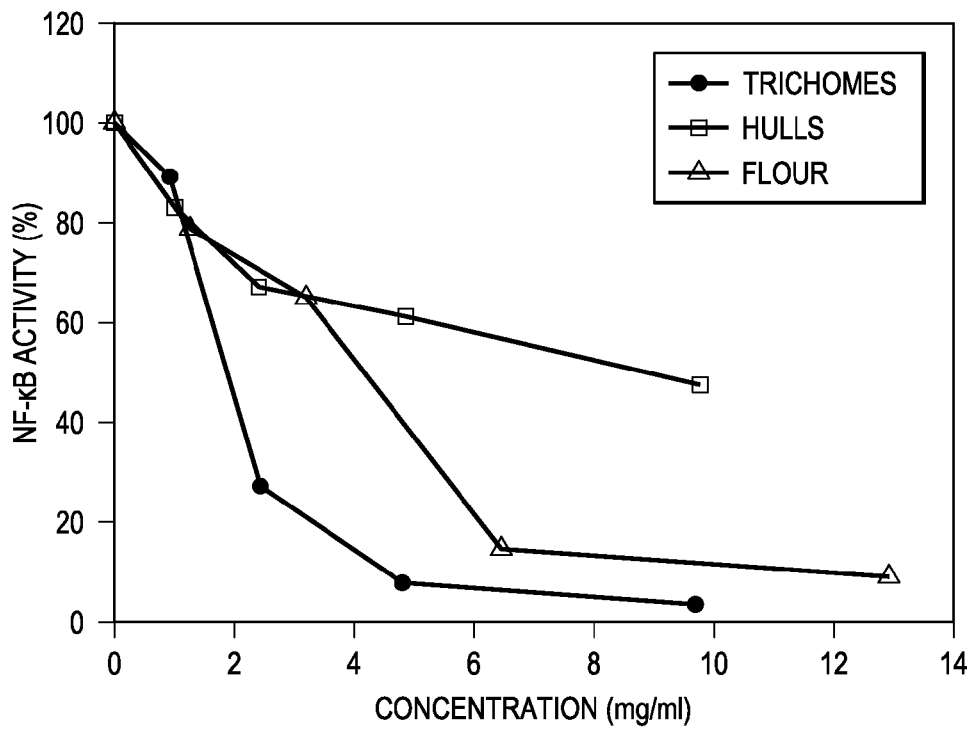
FIG. 2 is a graph depicting an effect of a selected oat fraction on NF-κB activity.

FIG. 2 is a graph depicting an inhibitory effect of a selected oat fraction on NF-κB activity. Each oat fraction caused a dose-response effect at inhibiting NF-κB activity, indicated by decreasing NF-κB activity levels with increasing concentrations of various oat fractions. As discussed above with respect to Table 3, oat trichomes were the most effective at inhibiting NF-κB activity, followed by oat flour, and then oat hulls.

Next, the inventors synthesized an avenanthramide ingredient from pure avenanthramides which had 2c:2p:2f in ratios that were similar to the ratios found in the various oat fractions. The NF-κB assay showed that the 2c:2p:2f ratio of about 1:2:2 was the most effective at inhibiting NF-κB activity. The 1:1:2 ratio was the next most effective, followed by the 1:1:1 ratio. These results are presented in Table 4 and are consistent with the experiment run using the various oat fractions, as shown in Table 3 and FIG. 2.

TABLE 4

| Avenanthramide Ratio (2c:2p:2f) | $IC_{50}$ (μM) |
|---|---|
| 1:1:1 | 56.55 A* |
| 1:1:2 | 34.44 B |
| 1:2:2 | 12.12 C |

*Values with different letters are significantly different from each other ($p < 0.05$).

Figure 3:
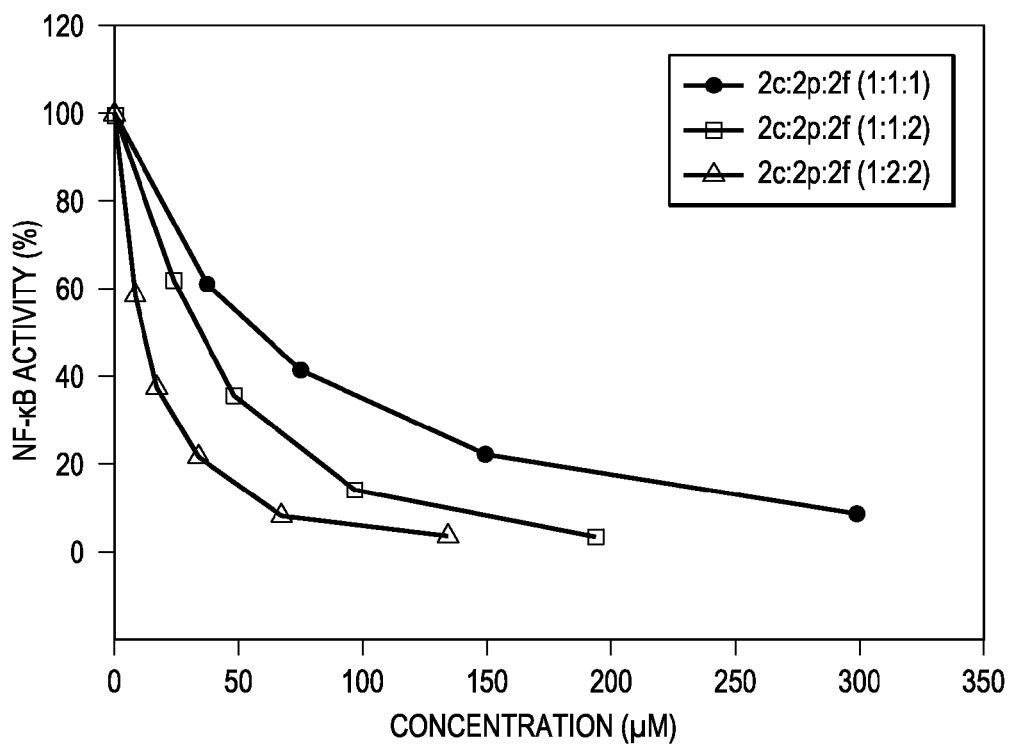
FIG. 3 is a graph depicting an effect of a synthesized avenanthramide ingredient with differing ratios of 2c:2p:2f, and its effect on NF-κB activity.

FIG. 3 is a graph depicting an effect of a synthesized avenanthramide ingredient having specific ratios of 2c:2p:2f on NF-κB activity. The effect of avenanthramide ratios (2c:2p:2f) on inhibiting NF-κB activity were investigated to provide a potential explanation for the effect observed with oat trichomes. Each avenanthramide ratio demonstrated a similar dose-response effect at inhibiting NF-κB activity as shown in FIG. 2. The 1:2:2 ratio, which is similar to the oat trichome avenanthramide ratio, was the most effective at inhibiting NF-κB activity, with an $IC_{50}$ of 12.12 μM, followed by the flour ($IC_{50}$=34.44 μM) and then the hulls ($IC_{50}$=56.55 μM). These findings support the contention that the specific avenanthramide ratio in each oat fraction is causing the observed anti-inflammatory effect and that certain avenanthramide ratios are more effective than others. Importantly, inventors discovered that the actual amounts of avenanthramides were not responsible for causing these observed effects.

Using the novel results disclosed above, inventors propose creating an enriched, oat-based product by adding an avenanthramide ingredient having a predetermined ratio of avenanthramides 2c:2p:2f for achieving a desired health benefit. For example, the avenanthramide ingredient may be an oat fraction separated from raw oats using any currently existing or later developed separation techniques. Alternatively, the avenanthramide ingredient may be synthesized from pure avenanthramides having the unique ratios described herein. Specifically, the avenanthramide ingredient may have a ratio of avenanthramides 2c:2p:2f of about 1:1:1 or about 1:2:2 to achieve an optimal antioxidant or anti-inflammatory effect, respectively.

FIG. 4 is a flowchart of a method for producing an avenanthramide-enriched oat product in accordance with an illustrative embodiment. A desired health effect is identified from at least one of an anti-inflammatory effect and an antioxidant effect (step 402). An avenanthramide ingredient is derived based on the desired health effect identified in step 402 (step 404). In an illustrative embodiment, the avenanthramide ingredient may be derived from the separation of raw oat into one or more constituent fractions that includes oat hulls and oat trichomes. Alternatively, the derivation step may take the form of synthesizing an avenanthramide ingredient having a specific ratio of avenanthramides 2c:2p:2f corresponding to the health effect identified in step 402. For example, the avenanthramide ingredient may have avenanthramides 2c:2p:2f in a ratio of 1:1:1 for achieving an improved antioxidant effect. Likewise, the avenanthramide ingredient may be synthesized to include avenanthramides 2c:2p:2f in a ratio of 1:2:2 for achieving an improved anti-inflammatory effect.

In any event, the avenanthramide ingredient is added to the oat-based product (step 406). In an illustrative embodiment, adding can mean (1) using the derived avenanthramide ingredient to create an oat-based product, (2) augmenting a pre-existing amount of an oat-based ingredient with the derived avenanthramide ingredient, or (3) substituting any part or all of an existing oat-based ingredient with the derived avenanthramide ingredient.

Finally, in an optional step, processing of the oat-based product is completed (step 408). In a non-limiting example, this processing step may include further cooking the oat-based product, or simply packaging the oat-based product for delivery.

The flowchart in the figure provided above illustrates a method for producing an avenanthramide-enriched, oat-based product with optimal health benefits. Each block in the flowchart may represent a step in an overall process. In some alternative implementations, the steps in the various blocks may occur out of order provided in the figures. For example, two blocks in a flowchart that are shown in succession may actually be implemented substantially concurrently. Alternatively, the steps depicted in two successive blocks may actually be executed in a reverse order, depending upon a particular implementation.

Inflammation and oxidative stress play critical roles in the pathogenesis of many diseases, such as cancer, cardiovascular disease, arthritis, and obesity. The inhibition of NF-κB activity is a key step in suppressing inflammation and therefore preventing disease formation. Likewise, the presence of antioxidants prevents cellular damage by interacting with reactive oxygen species to terminate the otherwise harmful chain reactions that these unstable molecules set into motion. With this knowledge, the inventors set out to determine the impact of specific avenanthramide ratios on inflammation and antioxidant activity. It has been discovered that the avenanthramide ratio of about 1:2:2, which is similar to what is found in oat trichomes, was demonstrated to be the most effective at inhibiting NF-κB activity. Additionally, avenanthramides 2c:2p:2f in a ratio of about 1:1:1, which can be found in oat hulls, was demonstrated to have the highest antioxidant activity. Either ratio could be incorporated into oat food products in order to increase the health beneficial effects of the product through the addition of an avenanthramide ingredient derived synthetically, from one or more breeding processes, or from the separation of oat fractions from raw oats.

While this invention has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ADDITIONAL DESCRIPTION

In a first aspect, the invention is an oat-based food product having an avenanthramide ingredient with avenanthramides 2c:2p:2f in the ratio of about 1:1:1.

Another embodiment including any one or more of the elements in a previous embodiment disclosed above wherein the avenanthramide ingredient is derived from an oat hull fraction separated from raw oat.

Another embodiment including any one or more of the elements in a previous embodiment disclosed above wherein the avenanthramide ingredient is a synthesized additive having the avenanthramides 2c:2p:2f in the ratio of about 1:1:1.

In another aspect, the invention is an oat-based food product having an avenanthramide ingredient with avenanthramides 2c:2p:2f in the ratio of about 1:2:2.

Another embodiment including any one or more of the elements in a previous embodiment disclosed above wherein the avenanthramide ingredient is derived from an oat trichome fraction separated from raw oat.

Another embodiment including any one or more of the elements in a previous embodiment disclosed above wherein the avenanthramide ingredient is a synthesized additive having the avenanthramides 2c:2p:2f in the ratio of about 1:2:2.

In a third aspect, the invention is a method for producing an avenanthramide-enriched, oat-based product with an improved health effect. The method generally includes the steps of deriving an avenanthramide ingredient having a pre-selected ratio of 2c:2p:2f; and adding the avenanthramide ingredient to the oat product to achieve the improved health effect.

Another embodiment including any one or more of the elements in a previous embodiment disclosed above wherein the method includes a step of identifying the improved health effect from at least one of an antioxidant effect and an anti-inflammatory effect; and then performing the deriving step to achieve the improved health effect.

Another embodiment including any one or more of the elements in a previous embodiment disclosed above wherein the deriving step further comprises separating a raw oat into a set of constituent fractions, wherein the set of constituent fractions comprise at least one of oat hulls and oat trichomes.

Another embodiment including any one or more of the elements in a previous embodiment disclosed above wherein deriving the avenanthramide ingredient further comprises creating a synthesized additive having avenanthramides 2c:2p:2f in a ratio of about 1:1:1.

Another embodiment including any one or more of the elements in a previous embodiment disclosed above wherein deriving the avenanthramide ingredient further comprises creating a synthesized additive having avenanthramides 2c:2p:2f in a ratio of about 1:2:2.

Another embodiment including any one or more of the elements in a previous embodiment disclosed above wherein the avenanthramide ingredient comprises at least one of oat hulls or a synthesized additive having avenanthramides 2c:2p:2f in a ratio of about 1:1:1.

Another embodiment including any one or more of the elements in a previous embodiment disclosed above wherein the avenanthramide ingredient comprises at least one of oat trichomes or a synthesized additive having avenanthramides 2c:2p:2f in a ratio of about 1:2:2.

Another embodiment including any one or more of the elements in a previous embodiment disclosed above wherein deriving an avenanthramide ingredient having a pre-selected ratio of 2c:2p:2f further comprises combining two or more oat fractions to achieve the pre-selected ratio of 2c:2p:2f, wherein the two or more oat fractions are selected from oat hulls, oat trichomes, and oat flour.

We claim:

1. An oat product enriched with an added pre-selected ratio of avenanthramides 2c:2p:2f, the enriched oat product comprising:

an avenanthramide ingredient providing the pre-selected ratio of avenanthramides 2c:2p:2f, wherein the pre-selected ratio of avenanthramides 2c:2p:2f is about 1:1:1.

2. The enriched oat product of claim 1, wherein the avenanthramide ingredient is derived from an oat hull fraction separated from raw oat.

3. The enriched oat product of claim 1, wherein the avenanthramide ingredient is a synthesized additive.

4. An oat product enriched with an added pre-selected ratio of avenanthramides 2c:2p:2f, the enriched oat product comprising:

an avenanthramide ingredient providing the pre-selected ratio of avenanthramides 2c:2p:2f, wherein the pre-selected ratio of avenanthramides 2c:2p:2f is about 1:2:2.

5. The enriched oat product of claim 4, wherein the avenanthramide ingredient is derived from an oat trichome fraction separated from raw oat.

6. The enriched oat product of claim 4, wherein the avenanthramide ingredient is a synthesized additive.

7. A method for creating an enriched oat product with an improved health effect, the method comprising:

deriving an avenanthramide ingredient having a pre-selected ratio of 2c:2p:2f wherein the preselected ratio is selected from a ratio of about 1:1:1 and about 1:2:2; and adding the avenanthramide ingredient to the oat product to achieve the improved health effect.

8. The method of claim 7, further comprising:

identifying the improved health effect from at least one of an antioxidant effect and an anti-inflammatory effect; and performing the deriving step to achieve the improved health effect.

9. The method of claim 7, wherein deriving the avenanthramide ingredient further comprises separating a raw oat into a set of constituent fractions, wherein the set of constituent fractions comprise at least one of oat hulls and oat trichomes.

10. The method of claim 7, wherein deriving the avenanthramide ingredient further comprises creating a synthesized additive having avenanthramides 2c:2p:2f in a ratio of about 1:1:1.

11. The method of claim 7, wherein deriving the avenanthramide ingredient further comprises creating a synthesized additive having avenanthramides 2c:2p:2f in a ratio of about 1:2:2.

12. The method of claim 7, wherein the avenanthramide ingredient comprises at least one of oat hulls or a synthesized additive having avenanthramides 2c:2p:2f in a ratio of about 1:1:1.

13. The method of claim 7, wherein the avenanthramide ingredient comprises at least one of oat trichomes or a synthesized additive having avenanthramides 2c:2p:2f in a ratio of about 1:2:2.

14. The method of claim 7, wherein deriving an avenanthramide ingredient having a pre-selected ratio of 2c:2p:2f further comprises:

combining two or more oat fractions to achieve the pre-selected ratio of 2c:2p:2f, wherein the two or more oat fractions are selected from oat hulls, oat trichomes, and oat flour.

* * * * *